US011419730B2

(12) United States Patent
Johnson

(10) Patent No.: US 11,419,730 B2
(45) Date of Patent: Aug. 23, 2022

(54) ARTIFICIAL KNEE

(71) Applicant: Phillip W. Johnson, Blacksburg, VA (US)

(72) Inventor: Phillip W. Johnson, Blacksburg, VA (US)

( * ) Notice: Subject to any disclaimer, the term of this patent is extended or adjusted under 35 U.S.C. 154(b) by 0 days.

(21) Appl. No.: 16/678,919

(22) Filed: Nov. 8, 2019

(65) Prior Publication Data

US 2020/0146833 A1     May 14, 2020

Related U.S. Application Data

(60) Provisional application No. 62/758,478, filed on Nov. 9, 2018.

(51) Int. Cl.
*A61F 2/38* (2006.01)
*A61F 2/64* (2006.01)
*A61F 2/30* (2006.01)
*A61F 2/68* (2006.01)

(52) U.S. Cl.
CPC .............. *A61F 2/3836* (2013.01); *A61F 2/64* (2013.01); *A61F 2002/30433* (2013.01); *A61F 2002/30505* (2013.01); *A61F 2002/6854* (2013.01); *A61F 2220/0041* (2013.01)

(58) Field of Classification Search
CPC .......... A61F 2/3836; A61F 2002/30433; A61F 2002/30505; A61F 2/64; A61F 202/6854; A61F 2220/0041
See application file for complete search history.

(56) References Cited

U.S. PATENT DOCUMENTS

| | | | |
|---|---|---|---|
| 41,934 A | 3/1864 | Monroe |
| 1,153,532 A | 9/1915 | Apgar |
| 2,696,011 A | 12/1954 | Galdik |
| 3,461,464 A | 8/1969 | Lindgren |
| 4,312,080 A | 1/1982 | Staats |
| 4,459,709 A | 7/1984 | Leal et al. |
| 4,872,879 A | 10/1989 | Shamp |

(Continued)

OTHER PUBLICATIONS

D-Rev, ReMotion Knee, http://d-rev.org/projects/mobility/, retrieved Jun. 2, 2017 (4 pages).

(Continued)

*Primary Examiner* — Yashita Sharma
*Assistant Examiner* — Aren Patel
(74) *Attorney, Agent, or Firm* — Allan A. Fanucci

(57) ABSTRACT

An artificial knee that has first and second knee components connected together for rotation between a first, upright position and a second position where one knee component is positioned at an angle to the other, an alignment mechanism associated with the first and second knee components to assure rotation in a vertical plane from the first position to the second position, and a biasing member. One knee component includes an extension member located in a central location, while the other includes a centrally located slot that receives the extension member and allows rotation only in a vertical plane. The biasing member normally holds the knee components in the first position, such that rotation of the first knee component away from the second knee component stretches or elongates the biasing member to provide a force that urges the knee components to move back to the first position.

20 Claims, 10 Drawing Sheets

(56) References Cited

U.S. PATENT DOCUMENTS

| | | | |
|---|---|---|---|
| 4,911,709 | A | 3/1990 | Marlow et al. |
| 5,133,777 | A | 7/1992 | Arbogast et al. |
| 5,228,164 | A | 7/1993 | Graf et al. |
| 5,724,714 | A | 3/1998 | Love |
| 5,888,231 | A | 3/1999 | Sandvig et al. |
| 6,508,842 | B1 | 1/2003 | Caspers |
| 6,793,682 | B1 | 9/2004 | Mantelmacher |
| 7,153,327 | B1* | 12/2006 | Metzger ............ A61F 2/08 623/20.29 |
| 7,883,547 | B2 | 2/2011 | Mantelmacher |
| 8,313,534 | B1* | 11/2012 | Chen ............ A61F 5/0123 623/43 |
| 10,376,390 | B1 | 8/2019 | Johnson |
| 2004/0153168 | A1 | 8/2004 | Childress et al. |
| 2005/0015156 | A1* | 1/2005 | Hikichi ............ A61F 2/68 623/24 |
| 2005/0143839 | A1* | 6/2005 | Chen ............ A61F 2/644 623/39 |
| 2006/0173554 | A1 | 8/2006 | Slemker et al. |
| 2007/0055383 | A1 | 3/2007 | King |
| 2008/0133019 | A1* | 6/2008 | Andrysek ............ A61F 2/68 623/20.14 |
| 2010/0114331 | A1 | 5/2010 | Mantelmacher |
| 2010/0304205 | A1 | 12/2010 | Jo et al. |
| 2010/0305698 | A1* | 12/2010 | Metzger ............ A61F 2/3836 623/13.12 |
| 2011/0009981 | A1* | 1/2011 | Okuda ............ A61F 2/642 623/32 |
| 2014/0277584 | A1 | 9/2014 | Hurley et al. |
| 2018/0161180 | A1 | 6/2018 | Arelekatti |
| 2020/0297514 | A1 | 9/2020 | Prescott |

OTHER PUBLICATIONS

Williams, "Nonprofit Hope to Walk helping injured get back on their feet," The Roanoke Times, Mar. 26, 2016 (9 pages); http://www.roanoke.com/news/local/blacksburg/nonprofit-hope-to-walk-helping-injured-get-back-on-their/article_1ae3a731-e6bf-5bb6-aa93-09d2273d7bc2.html.

OConnor, "Johnson City man creates affordable prosthetics," News 5 WCYB, Sep. 30, 2015 (6 pages); http://www.wcyb.com/meet-the-term/kristi-oconnor/8196910).

Techform. Material Safety Data Sheet. Ossur, Jan. 2011. (in related U.S. Appl. No. 15/613,045, now U.S. Pat. No. 10,376,390.).

Össur, Modular Socket System—Direct Lamination, 2015. (in related U.S. Appl. No. 15/613,045, now U.S. Pat. No. 10,376,390.).

Össur, Össur Presents: Modular Socket System, YouTube video screen shot, Aug. 22, 2011. (in related U.S. Appl. No. 15/613,045, now U.S. Pat. No. 10,376,390.).

SPS PVA Bag, SPS Website; date verified by the wayback machine Mar. 7, 2016. (in related U.S. Appl. No. 15/613,045, now U.S. Pat. No. 10,376,390.).

* cited by examiner

ARTIFICIAL KNEE

CROSS-REFERENCE TO RELATED APPLICATIONS

This application claims the benefit of U.S. Provisional Application 62/758,478, filed Nov. 9, 2018, the entirety of which is herein incorporated by reference. This application is related to U.S. Nonprovisional application Ser. No. 15/613,045 ('045 application), filed Jun. 2, 2017, now U.S. Pat. No. 10,376,390, and U.S. Nonprovisional application Ser. No. 16/538,751, filed Aug. 12, 2019, which is a continuation-in-part application of the '045 application.

BACKGROUND

The present invention relates to artificial knee construction which have a simple, low cost design.

U.S. Pat. No. 4,614,518 discloses an artificial limb with automatic release for free rotation that can be used as an artificial knee. This device is very complicated and includes structures for providing both vertical rotation and horizontal movement. In addition to being complicated it is a costly device that is not affordable for poor or disadvantage persons. Accordingly, there is the need for an artificial knee that is both functional and available at a relatively low cost. This is now provided by the present invention.

SUMMARY OF THE INVENTION

The invention now provides an artificial knee comprising first and second knee components connected together for rotation between a first, upright position and a second position where one knee component is positioned at an angle to the other; an alignment mechanism associated with the first and second knee components to assure rotation in a vertical plane from the first position to the second position, and a biasing member. One of the first and second knee components includes an extension member located in a central location of that component, while the other component includes a centrally located slot configured and dimensioned to receive the extension member such that rotation is allowed only in the vertical plane as the extension member moves in the slot between the first and second positions. The biasing member is operatively associated with the first and second knee components for normally holding the knee components in the first position, such that rotation of the first knee component away from the second knee component stretches or elongates the biasing member to provide a force that urges the knee components to move back to the first position.

The first knee component typically comprises a first cylindrical member having a first end for receiving a rod member, while the second knee component typically comprises a first cylindrical member having a first end for receiving a rod member, and the first and second knee components are connected together by a horizontal bolt and nut for rotation of the knee components.

The artificial knee also may include a stop member configured and position such that the knee components can rotate only in one angular direction (i.e., clockwise or counterclockwise but not in both directions). Advantageously, the biasing member is an elastomeric member or a metal spring. As the knee components are typically made of plastic or aluminum, the biasing member can be attached to one or each knee component by a screw or bolt. Also, the first and second knee components are typically connected together by a horizontal bolt and nut that facilitates the rotation of the knee components.

The artificial knee of the present invention provides a lightweight, versatile, low cost device that can assist individuals that have lost a leg and is preferably used with artificial foot prostheses such as those disclosed in related application Ser. No. 15/613,045 ('045 application), filed Jun. 2, 2017, now U.S. Pat. No. 10,376,390, and Ser. No. 16/538,751, filed Aug. 12, 2019, which is a continuation-in-part application of the '045 application. This provides a much needed device to low income persons who could not otherwise afford to obtain a knee or leg prosthesis.

BRIEF DESCRIPTION OF THE DRAWINGS

The nature and various advantages of the present invention will become more apparent upon consideration of the following detailed description, taken in conjunction with the accompanying drawings, and in which.

DETAILED DESCRIPTION OF THE INVENTION

Figure 1:
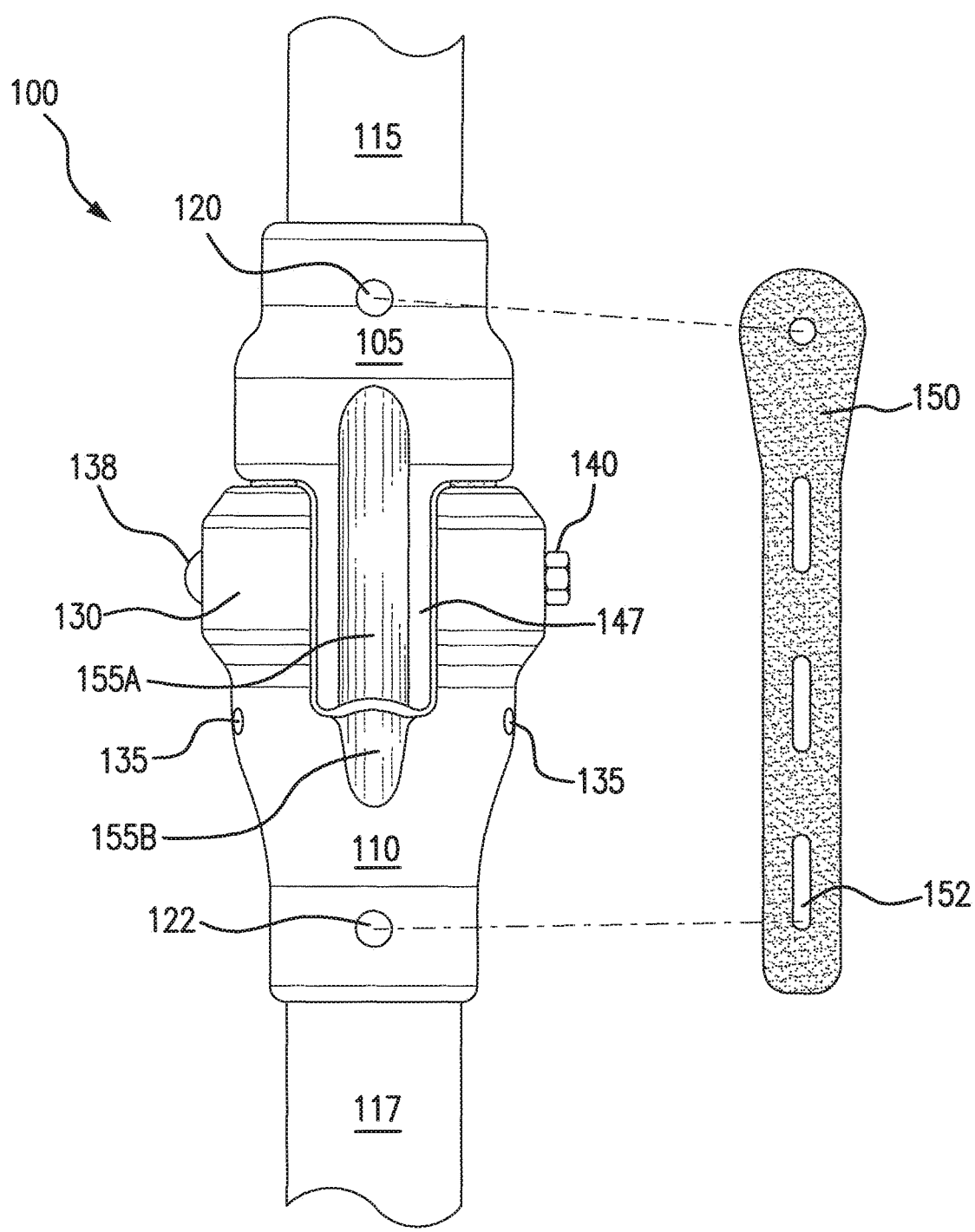
FIG. 1 is a front view of an artificial knee according to a first embodiment of the present invention.
Figure 2:
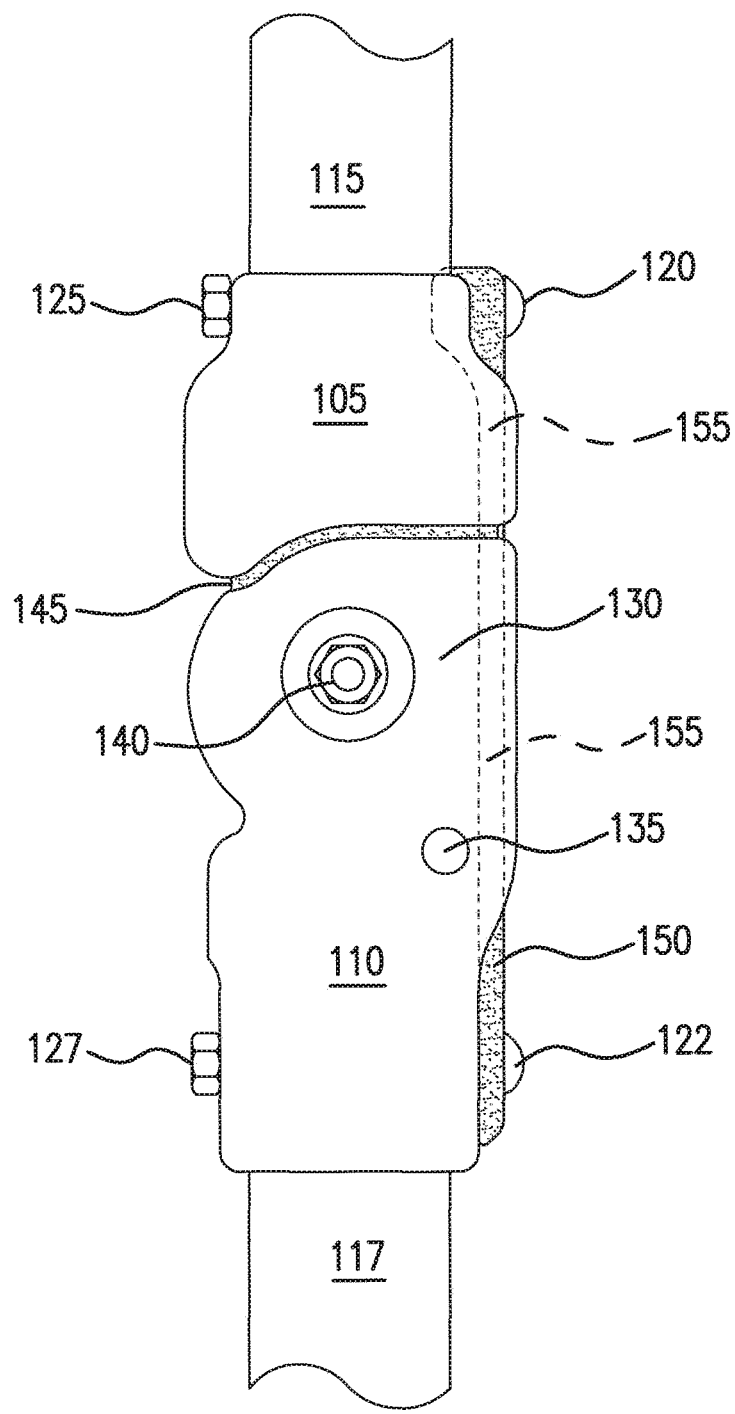
FIGS. 2 and 3 are side views of the artificial knee of FIG. 1, with the knee in extended and non-extended positions, respectively.
Figure 3:
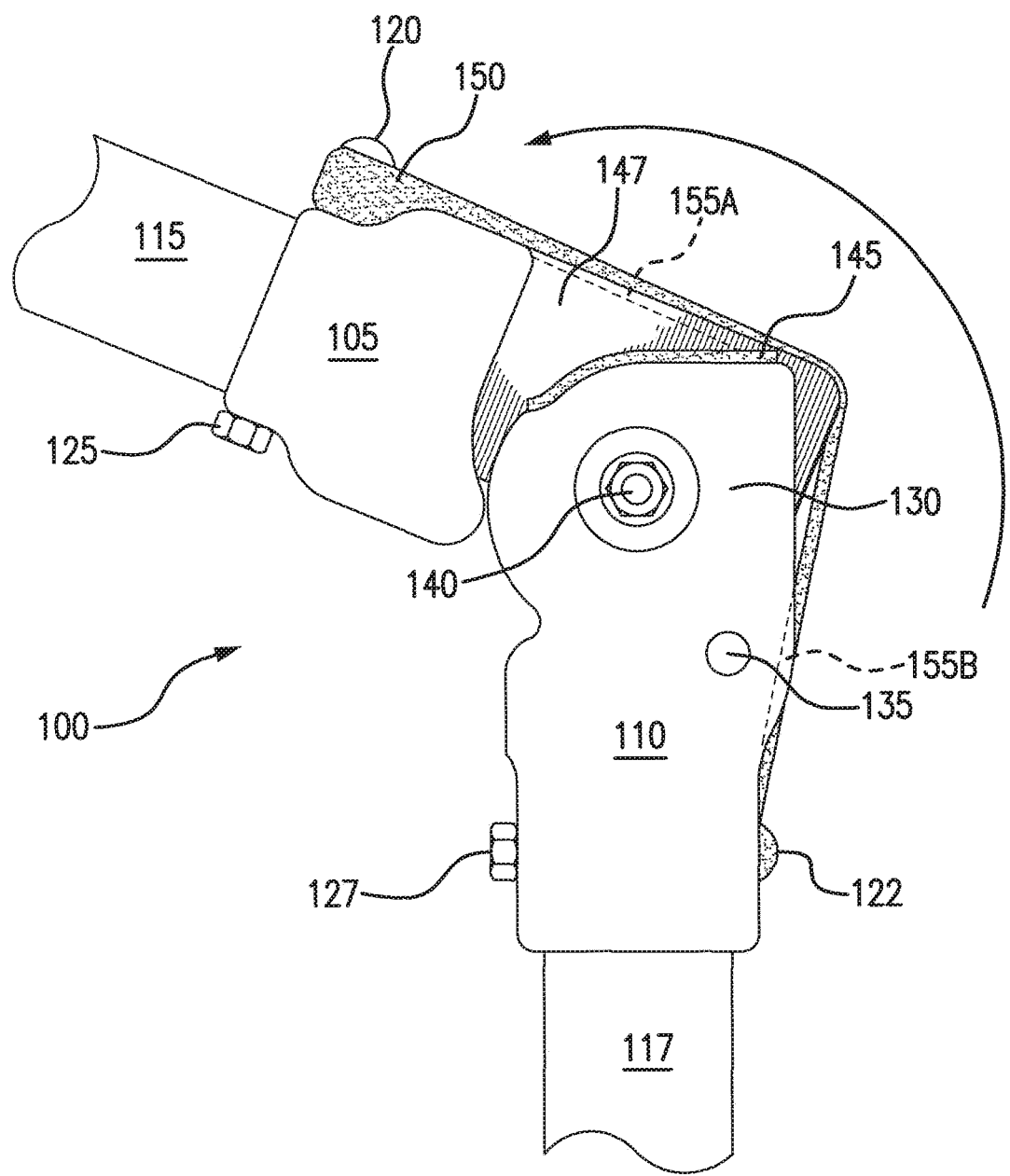
Figure 4:
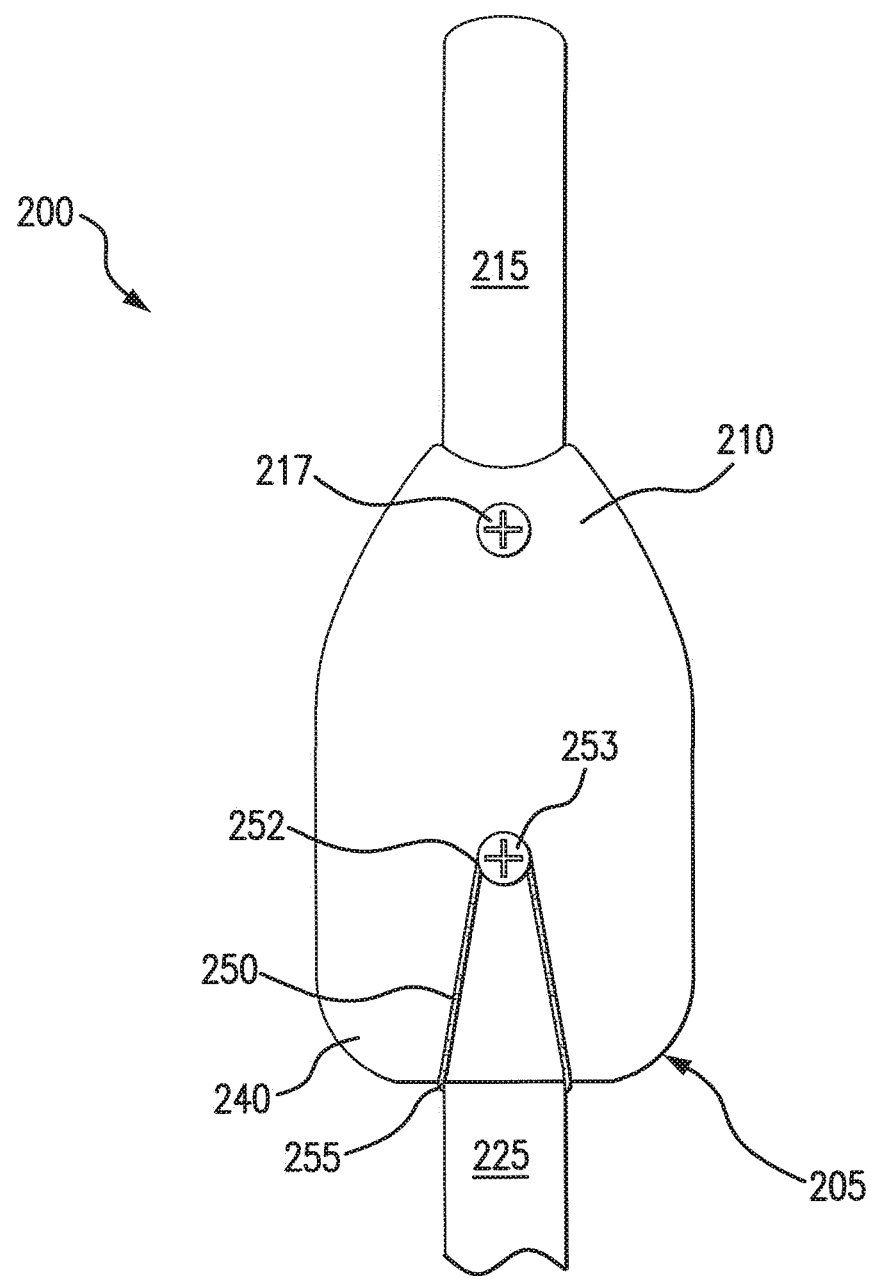
FIG. 4 is a front view of an artificial knee in accordance with a second embodiment of the present invention.
Figure 5:
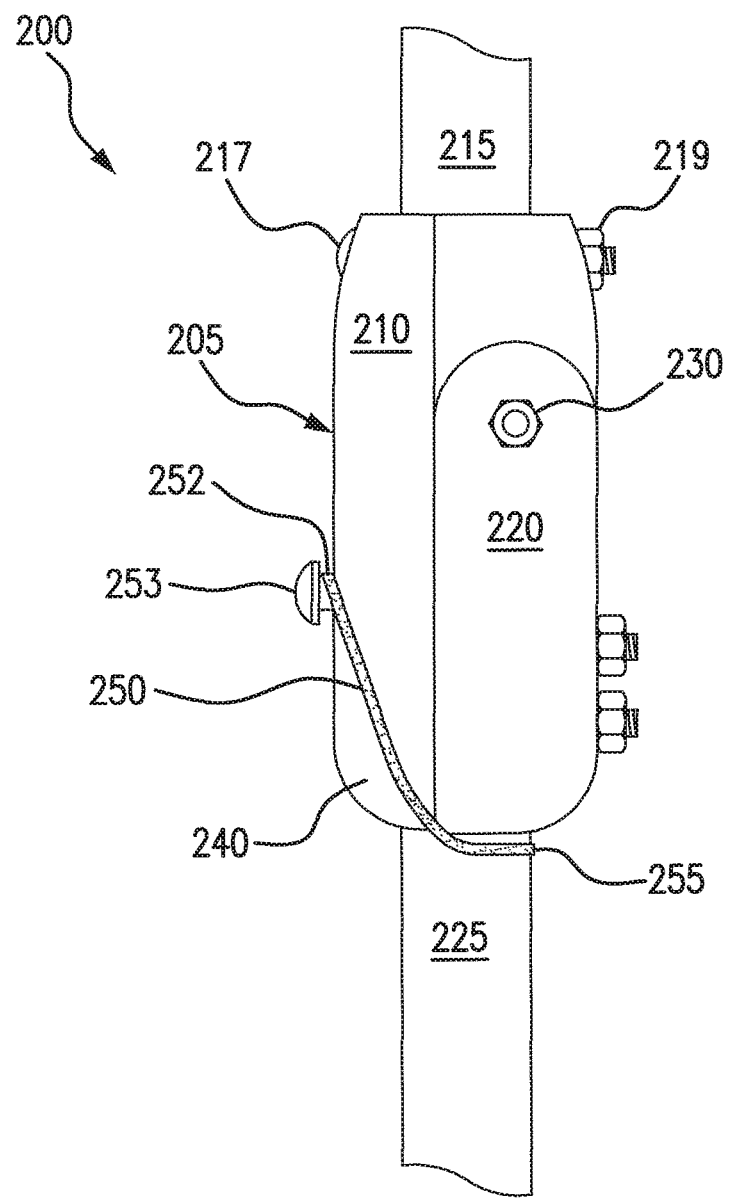
FIGS. 5 and 6 are side views of the artificial knee of FIG. 4, with the knee in extended and non-extended positions, respectively.
Figure 6:
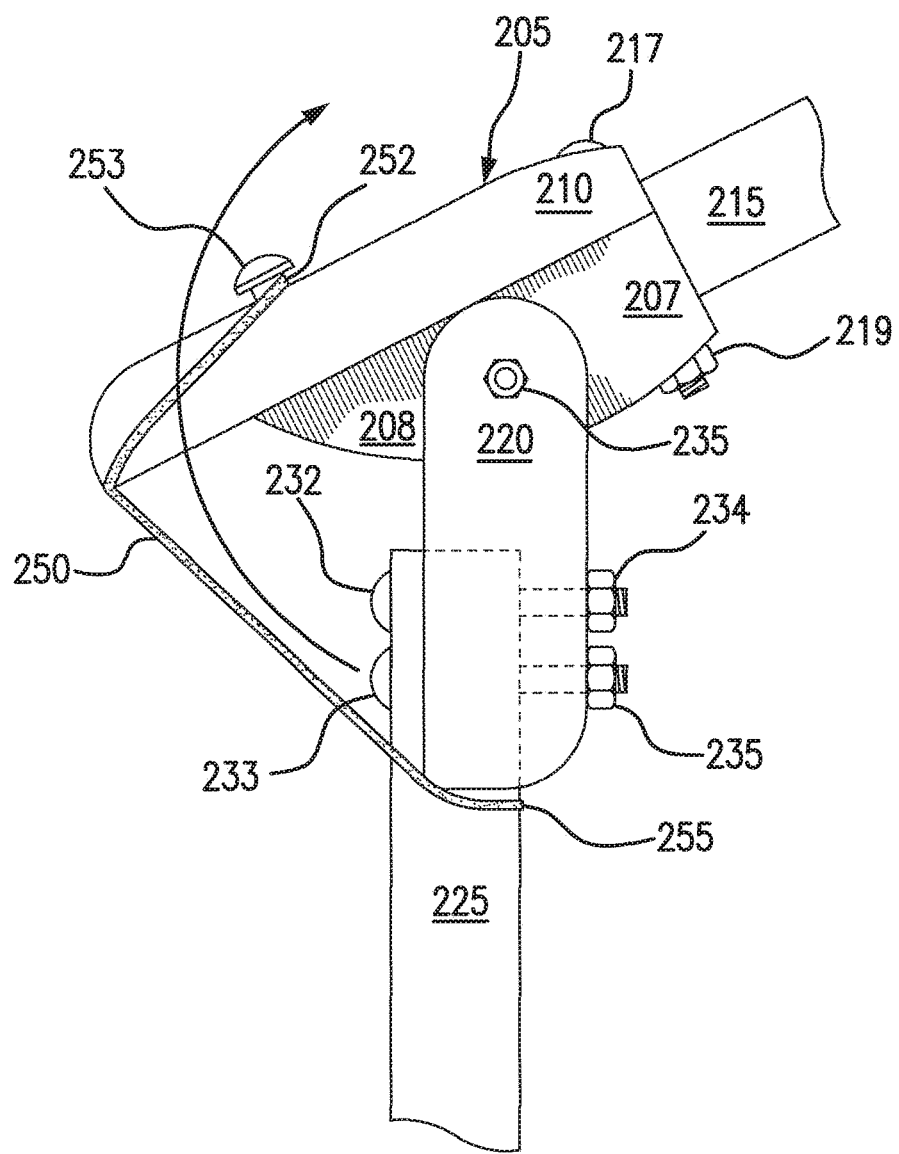

A number of embodiments of artificial knees are now provided by the present invention. FIGS. 1-3 illustrate a preferred embodiment where the artificial knee 100 includes an upper knee portion 105 and a lower knee portion 110. The upper portion 105 includes a cylindrical opening that can receive upper rod 115 that can be attached to a leg engaging member, while the lower portion 110 includes a cylindrical opening that can receive lower rod 117 that includes an artificial foot assembly. Leg engaging member and artificial foot assembly are as described in the inventor's related or copending application(s). A bolt and nut arrangement 120, 125 secures this cylindrical portion to the rod 115. A second bolt and nut arrangement 122, 127 secures this cylindrical portion to the rod 117.

Lower knee component 110 has a holding member 130 that has an opening that receives another bolt and nut arrangement 138, 140 that connects the lower knee portion 110 to the upper knee component 105 to allow vertical rotation. Lower knee component 110 also includes an opening 135 that can receive a locking member to immobilize the knee components from vertical movement.

The biasing member 150 is in the form of an elongated elastomeric member that has resiliency and stretchability and that connects the upper and lower knee members 105, 110 for vertical rotation. It also is received in a groove 155A, 155B that extends from the upper knee number 105 to the lower knee member 110 as shown best in FIG. 1. The biasing member 150 is connected to the upper and lower knee components 105, 110 by attachment to bolting 120 and 122, respectively.

The artificial knee of FIGS. 1-3 also includes an alignment mechanism in accordance with the invention. This includes an extension member 147 that extends away from the upper knee component 105 and that is received in a recess in the holding member 130 of the lower knee component 110. Extension member 147 extends away from the surface portion(s) of that knee component and is joined to the holding member by bolt and nut member 138, 140 and that construction facilitates the vertical rotation.

The artificial knee components of FIGS. 1-3 include surface portions configured for surface to surface contact when the components are in the first position. The knee component contact surface portions are in surface to surface contact in the first position when the artificial knee is upright, while these surfaces are spaced apart in the second position when the knee is flexed in use such as when the person that is wearing the knee is walking. The knee components move in only one rotational direction clockwise or counterclockwise depending upon what side of the artificial knee one is observing, but the surface to surface contact of the knee components act as a stop member to prevent further rotation of the knee components relative to each other in the other rotational direction. This prevents the person from falling forward over the artificial knee when walking.

The artificial knee of this embodiment can also include a dampening member provided on at least one knee component or on a plurality or all contact portions of both knee components to dampen contact between the knee components upon returning to the first position. In the artificial knee of FIGS. 1-3, the dampening member 145 is shown on the contact portions of the holding member 130 of the lower knee component 110. An additional dampening member can be provided on the contact portion of upper knee component if desired for greater dampening of the knee components when they contact each other at their respective contact portion surfaces. These dampening members can be used in any artificial knee embodiment of the present invention that includes contact portions in the knee components or contacting surfaces between them.

For the embodiment of FIGS. 1-2, the biasing member is an elastomeric member 150 having a first end attached to one knee component by a screw or bolt and a second end attached to the other knee component by a screw or bolt. The elastomeric member 150 includes at least one slot 152 for accommodating the screw or bolt at one end but can include a number of slots or other openings if desired for easier connect and adjustability for proper operation. The elastomeric member 150 is also configured and arranged for contacting both the first and second knee components 105, 110 when in the second position. For this embodiment, the elastomeric member 150 is received in grooves 155A, 155B. This helps in the stretching and elongation of the elastomeric member 150 and by having it in contact with the knee, catching of the user's fingers or other materials between the elastomeric member 150 and knee is minimized or avoided.

If desired, the artificial knee can include a locking member connecting the first and second knee components 105, 110 for retaining the knee components in the first position. This could be done when the components are shipped or to immobilize the leg in certain situations. The locking member passes through the opening 135 that passes through the holding member 130 and extension member 147 for the artificial knee of FIGS. 1-3.

In another embodiment, as shown in FIGS. 4-8B, the artificial knee 200 includes a first knee component 210 comprising a first elongated member 205 having a first end 210 for receiving part, approximately half, of an upper rod member 215 and a mating second member 207 for receiving the remaining part, approximately half, of the upper rod member 215. These members 205, 207 are secured to the rod member 215 by at least one horizontal bolt 217 and nut 219 arrangement, wherein the bolt 217 passes through holes 216 of the second member 207, through holes in the rod member 215 and then through hole 218 of the first end 210 of the first elongated member 205. Although one bolt and nut is shown, two can be used for greater strength if desired.

The second knee component 220 comprises a half cylindrical member for receiving half of a lower rod member 225, and the first and second knee components 210, 220 are connected together by a horizontal bolt 230 and nut 235 for rotation of the knee components. The second knee component 220 includes first and second upstanding wall members 222, 224 with respective holes 221, 223 for receiving bolt 230. The second member 207 of the first elongated member 205 includes a lower extension member 208 having a bore or hole 209. Bolt 230 passes through hole 209 after passing through hole 221 of the second member 207, and then through hole 223 of the first end 210 of the first elongated member 205. Of course, the holes are aligned to receive the bolt. Nut 235 is then applied to complete the attachment of the components for vertical rotation.

The second end 240 of the first elongated member 205 of the first knee component 210 includes a half cylindrical member 241 which is located opposite to and adjacent the half cylindrical member 245 of the second knee component 240 to sandwich and contact the rod member 225 therebetween. This forms a compact arrangement of the artificial knee for the wearer. The half cylindrical member 245 of the second knee component 220 is securely attached to the lower rod member 225 by a pair of horizontal bolts 232, 233, and nuts 234, 235, respectively.

For the embodiment of FIGS. 4-8A, the biasing member is an elastomeric or heavy rubber band 250 having one end 252 wrapped around a bolt or screw 253 located on the first elongated member 205 with the opposite end 255 placed around rod member 225. The biasing member 250 is also configured and arranged for contacting both the first and second knee components when in the second position. This helps in the stretching and elongation of the biasing member 250 and by having it in contact with the knee components, catching of the user's fingers or other materials between the expanded band and knee is minimized or avoided.

Figure 7:
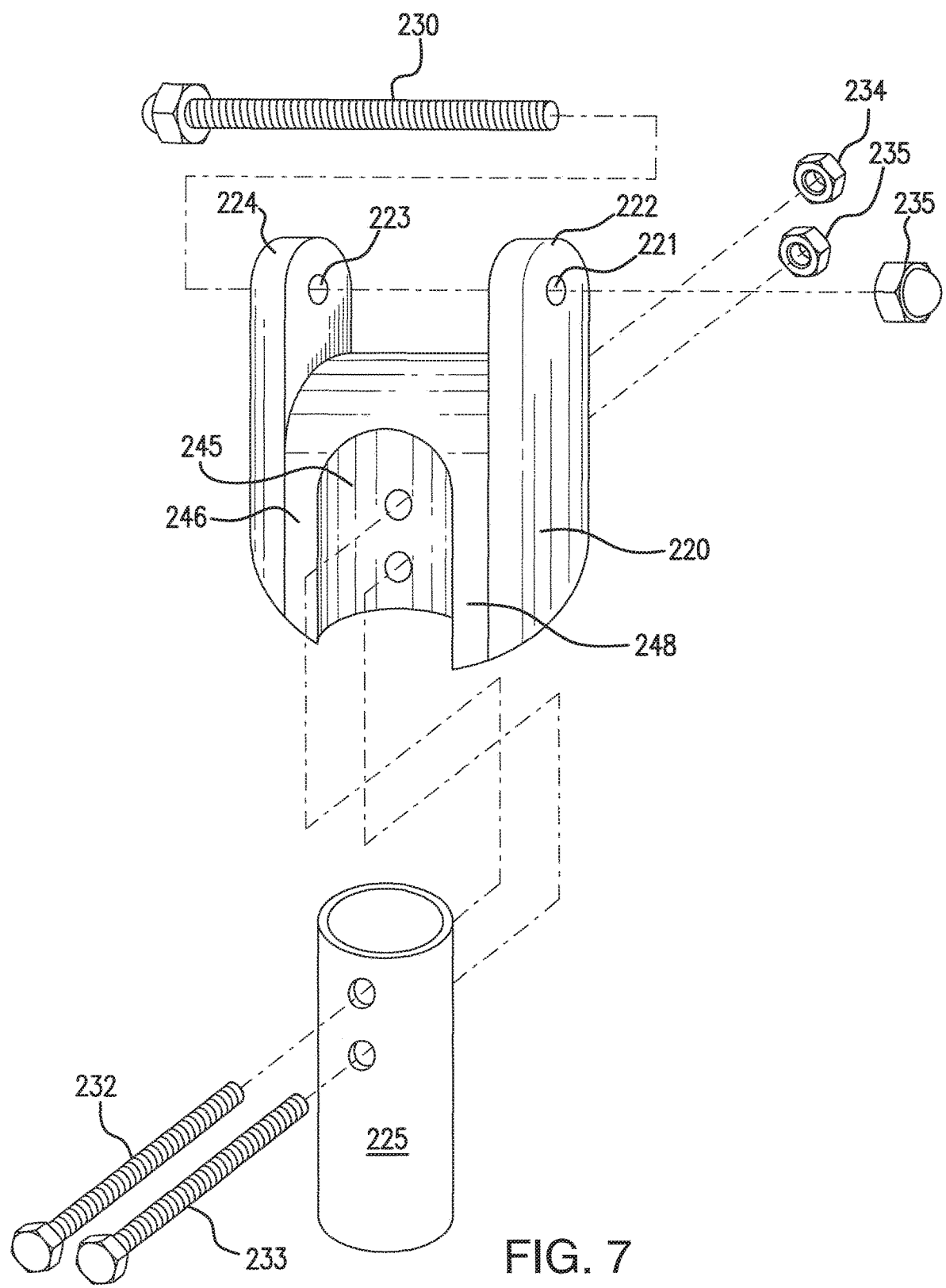
FIG. 7 is an exploded view of the lower knee component of the artificial knee of FIG. 4.
Figure 8A:
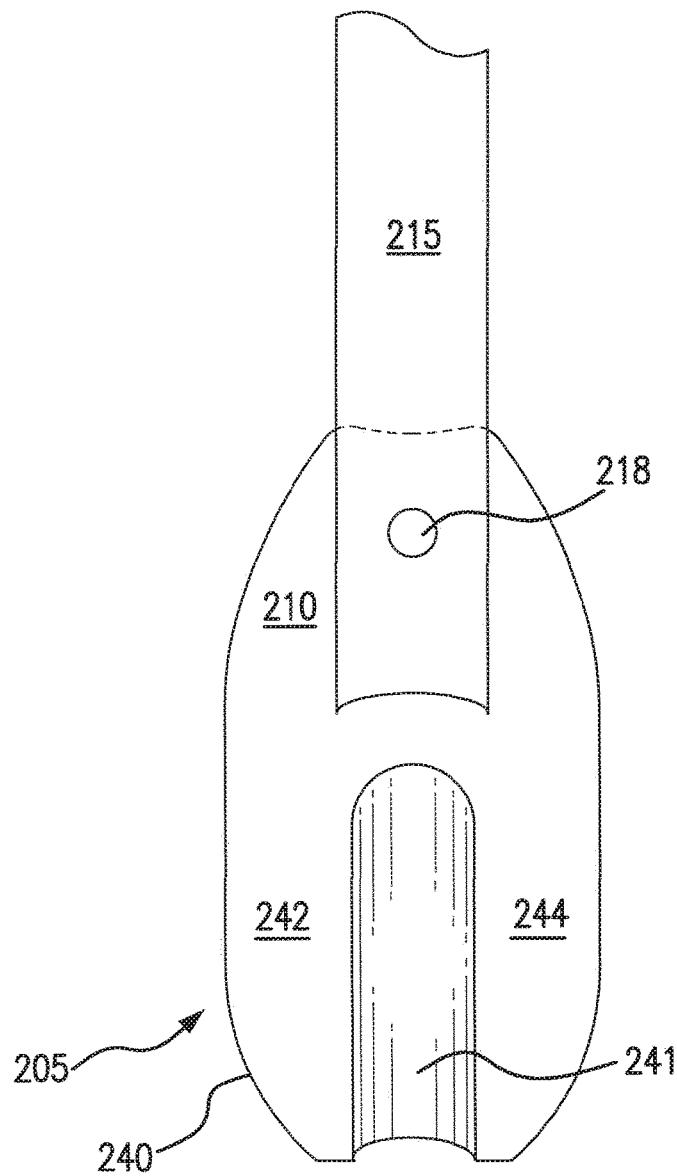
FIG. 8A is a back view of a front part of the first knee component of the artificial knee of FIG. 4.
Figure 8B:
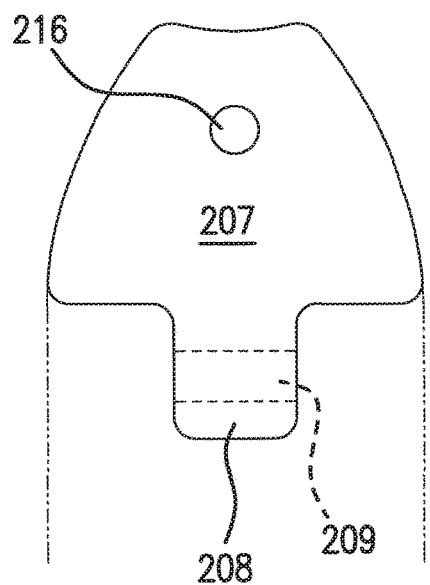
FIG. 8B is a back view of a rear part of the first knee component of the artificial knee of FIG. 4.

As in the prior embodiment, the first knee component may include one or more contact surfaces. FIGS. 7 and 8A best illustrate this. The second end 240 of the first elongated member 205 of the first knee component 210 includes two contact surfaces 242, 244 which engage contact surfaces 246, 248 of the second knee component 220 when the knee is vertical and not extended. Alternatively, a contact surface can be positioned and located on the lower extension member 208 of the second member 207 to contact an upper portion of the rod member 225 that is received in the half cylindrical member to act as a stop member to prevent further rotation of the knee components relative to each other in the opposite rotational direction from that which is provided for proper operation of the knee.

If desired, one or more dampening members can be applied to one or more of the contact surfaces 242, 244, and/or 246, 248. Material selection can also be made to provide dampening with the knee components made of a suitable plastic or rigid elastomeric material so that dampening members are not needed. The overall design will be dictated by patient comfort when walking, as dampening members can be added after the knee if placed on the patient if additional comfort is desired.

Figure 9:
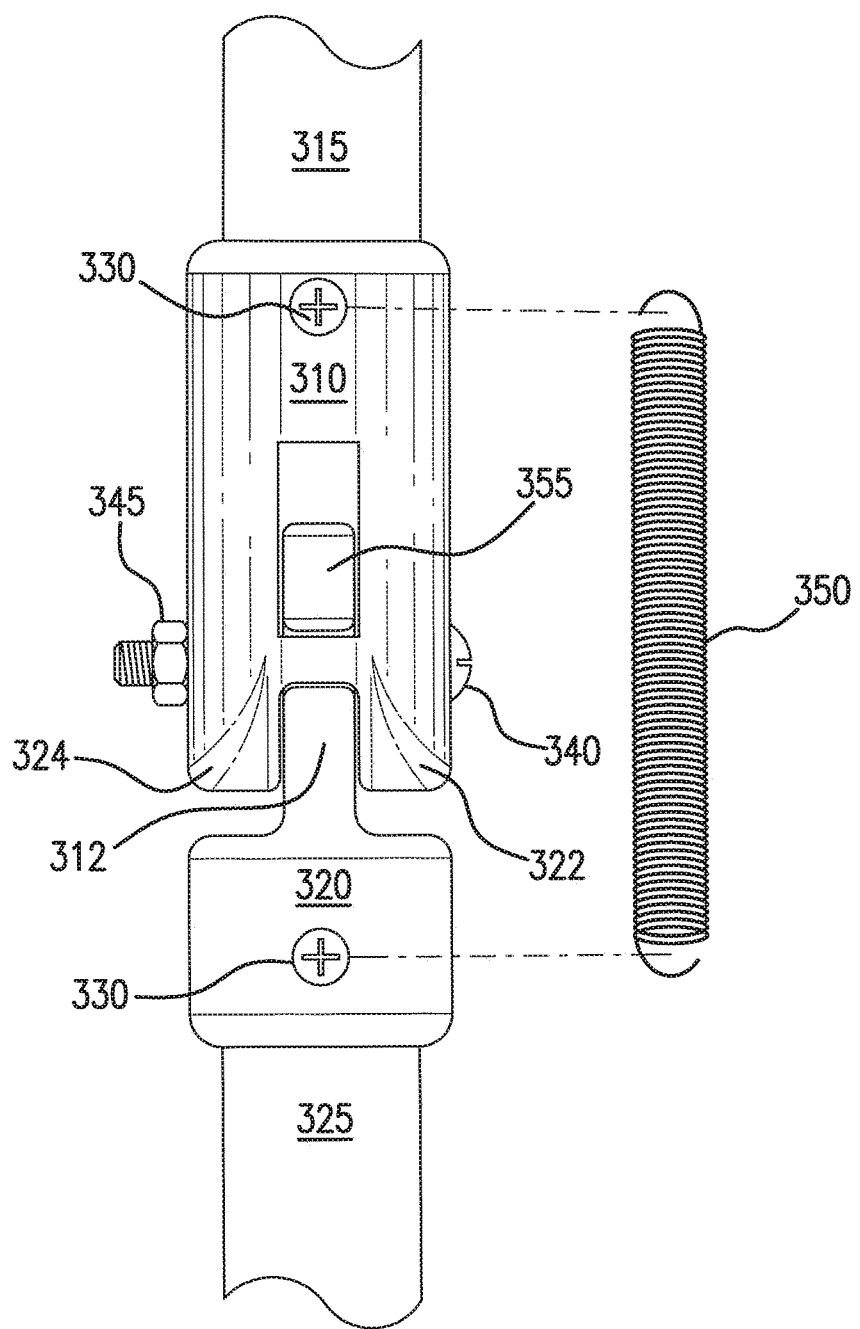
FIG. 9 is a front view of an artificial knee in accordance with the third embodiment of the present invention.
Figure 10:
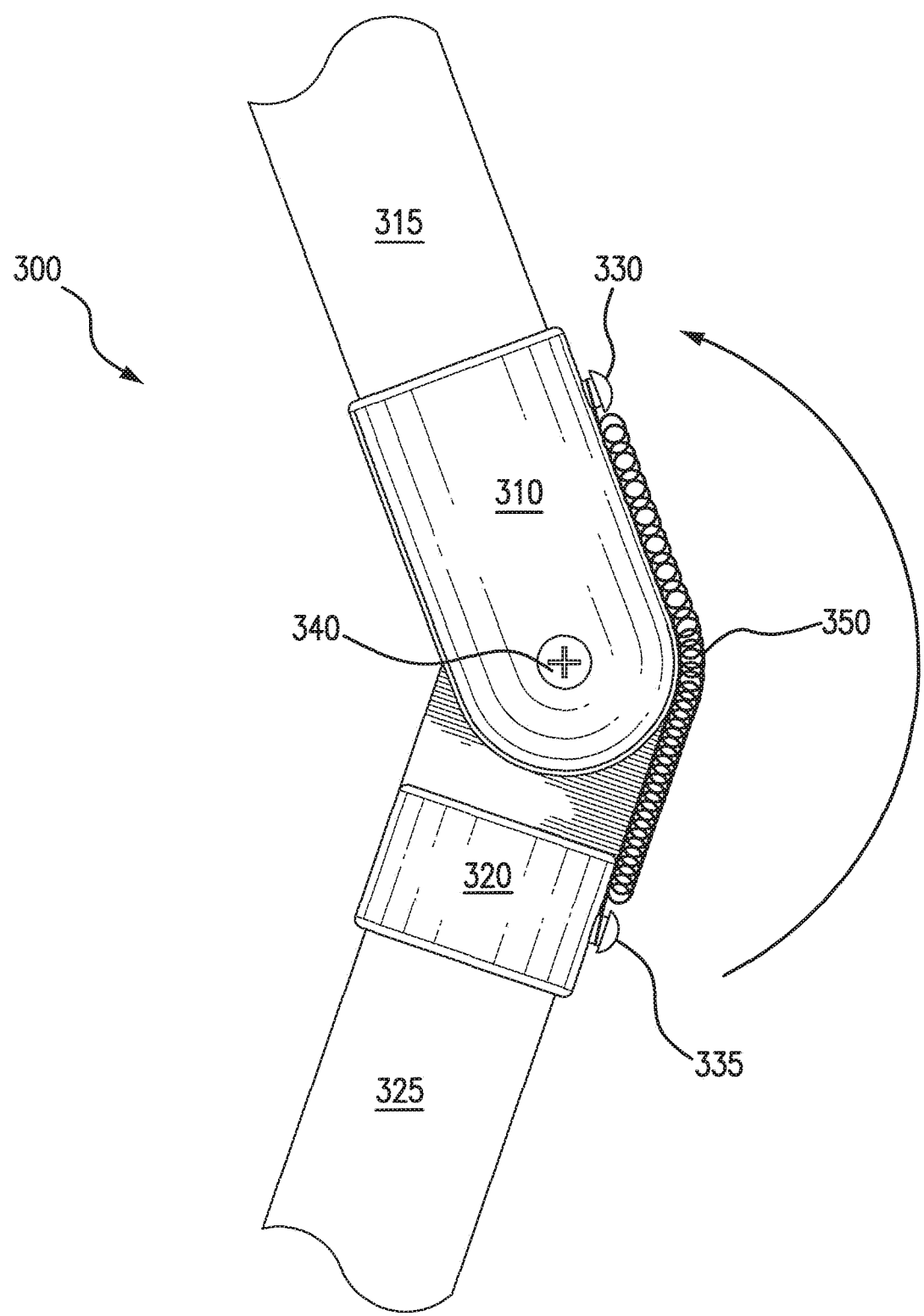
FIG. 10 is a side view of the artificial knee of FIG. 9.

In a further embodiment, as shown in FIGS. 9 and 10, a relatively simple artificial knee 300 is provided. This knee has a first, upper knee component 310 is a cylindrical member having an upper end to receive an upper rod 315 and a second, lower knee component 320 that also is a cylindrical member having a lower end that is attached to a lower rod 325. The ends of these knee components are secured to the rods by metal screws 330, 335, respectively.

The second knee component 320 has a second end that includes a pair of side walls 322, 324 surrounding a centrally located U-shaped recess, while a wall member 312 of the second knee component 320 is received in the U-shaped recess. These knee components are thus joined together by a bolt 340 and nut 345 arrangement. The bolt 340 passes through side walls 322, 324 and an opening or hole in the extension member 312. This forms an alignment mechanism with the wall member 312 that extends between and away from the first and second surface portions on the second end of the cylindrical member of the first knee component 310, and the slot that is provided by the U-shaped recess between the wall members 322, 324 on the second end of the cylindrical member of the second knee component 320. A stop member 355 is provided to prevent forward rotation of the knee components.

The biasing member 350 for this knee 300 is a simple metal spring that is connected to each of the cylindrical members of the first and second knee components 310, 320 by a screw or bolt 330, 335, wherein the metal spring is optionally provided within a sleeve to protect against pinching of fingers as the spring contracts from the second to first positions.

It is to be understood that additional embodiments of the present invention described herein may be contemplated by one of ordinary skill in the art and that the scope of the present invention is not limited to the embodiments disclosed. While specific embodiments of the present invention have been illustrated and described, numerous modifications come to mind without significantly departing from the spirit of the invention, and the scope of protection is only limited by the scope of the accompanying claims.

What is claimed is:

1. An artificial knee comprising:
   first and second knee components connected together for rotation between a first, upright position and a second position where one of the first and second knee components is positioned at an angle to the other one of the first and second knee components;
   an alignment mechanism associated with the first and second knee components to assure rotation in a vertical plane from the first position to the second position, wherein one of the first and second knee components includes an extension member located in a central location of that component, while the other component includes a centrally located slot configured and dimensioned to receive the extension member such that rotation is allowed only in the vertical plane as the extension member moves in the slot between the first and second positions;
   one or more contact portions associated with each knee component and configured for surface to surface contact when the knee components are in the first position, wherein the contact portions act as a stop member such that the knee components can rotate only in one angular direction;
   a dampening member provided on at least one contact portion to dampen contact between the knee components when returning to the first position; and
   a biasing member comprising an elastomeric member or rubber band operatively associated with the first and second knee components for holding the knee components in the first position, such that rotation of the first knee component away from the second knee component stretches or elongates the biasing member to provide a force that urges the knee components to move back to the first position;
   wherein the knee components are made of plastic and connected together by a horizontal bolt and nut that passes though the extension member in the slot to facilitate the rotation of the knee components.

2. The artificial knee of claim 1, wherein the first knee component comprises a first cylindrical member having an end for receiving a rod member, and the second knee component comprises a second cylindrical member having an end for receiving a rod member.

3. The artificial knee of claim 1, further comprising a locking member connecting the first and second knee components for retaining the knee components in the first position.

4. An artificial knee comprising:
   first and second knee components connected together for rotation between a first, upright position and a second position where one of the first and second knee components is positioned at an angle to the other one of the first and second knee components;
   an alignment mechanism associated with the first and second knee components to assure rotation in a vertical plane from the first position to the second position, wherein one of the first and second knee components includes an extension member located in a central location of that component, while the other component includes a centrally located slot configured and dimensioned to receive the extension member such that rotation is allowed only in the vertical plane as the extension member moves in the slot between the first and second positions;
   a biasing member operatively associated with the first and second knee components for holding the knee components in the first position, such that rotation of the first knee component away from the second knee component stretches or elongates the biasing member to provide a force that urges the knee components to move back to the first position; and
   one or more contact portions associated with each knee component and configured for surface to surface contact when the knee components are in the first position,
   wherein the biasing member is an elastomeric member or rubber band having a first end attached to one of the knee components by a screw or bolt and a second end attached to the other one of the knee components by a screw or bolt, and
   wherein the biasing member includes at least one slot for accommodating the screw or bolt and is configured and arranged for contacting both the first and second knee components when in the second position.

5. The artificial knee of claim 4, further comprising a locking member connecting the first and second knee components for retaining the knee components in the first position.

6. The artificial knee of claim 4, wherein the first knee component comprises a first cylindrical member having an end for receiving a rod member, the second knee component comprises a second cylindrical member having an end for receiving a rod member, and the first and second knee components are connected together by a horizontal bolt and nut for rotation of the knee components.

7. An artificial knee comprising:
first and second knee components connected together for rotation between a first, upright position and a second position where one of the first and second knee components is positioned at an angle to the other one of the first and second knee components;
an alignment mechanism associated with the first and second knee components to assure rotation in a vertical plane from the first position to the second position, wherein one of the first and second knee components includes an extension member located in a central location of that component, while the other component includes a centrally located slot configured and dimensioned to receive the extension member such that rotation is allowed only in the vertical plane as the extension member moves in the slot between the first and second positions; and
a biasing member operatively associated with the first and second knee components for holding the knee components in the first position, such that rotation of the first knee component away from the second knee component stretches or elongates the biasing member to provide a force that urges the knee components to move back to the first position;
wherein the first knee component comprises a first elongated member having a first end for receiving a rod member, the second knee component comprises a second member for receiving a rod member, and the first and second knee components are connected together by a horizontal bolt and nut for rotation of the knee components.

8. The artificial knee of claim 7, wherein the second member of the second knee component comprises is a half cylindrical member for receiving half of a rod member, and the first elongated member of the first knee component further comprises a second end that is located adjacent the half cylindrical member of the second knee component to sandwich and contact the opposite half of the rod member that is held by the half cylindrical member of the second knee component.

9. The artificial knee of claim 8, wherein the first knee component has a contact surface positioned and located to contact an upper portion of the rod member that is received in the half cylindrical member to act as a stop member to prevent further rotation of the knee components relative to each other.

10. The artificial knee of claim 7, wherein the extension member of the first knee component has a hole and the second knee component includes two upstanding wall members that each includes a hole, wherein the holes are aligned to receive the bolt that allows rotation of the knee components.

11. The artificial knee of claim 7, wherein the biasing member comprises an elastomeric member or rubber band.

12. The artificial knee of claim 7, wherein the first knee component comprises a first cylindrical member having an end for receiving a rod member, and the second knee component comprises a second cylindrical member having an end for receiving a rod member.

13. The artificial knee of claim 7, further comprising a locking member connecting the first and second knee components for retaining the knee components in the first position.

14. An artificial knee comprising:
first and second knee components connected together for rotation between a first, upright position and a second position where one of the first and second knee components is positioned at an angle to the other one of the first and second knee components;
an alignment mechanism associated with the first and second knee components to assure rotation in a vertical plane from the first position to the second position, wherein one of the first and second knee components includes an extension member located in a central location of that component, while the other component includes a centrally located slot configured and dimensioned to receive the extension member such that rotation is allowed only in the vertical plane as the extension member moves in the slot between the first and second positions; and
a biasing member operatively associated with the first and second knee components for holding the knee components in the first position, such that rotation of the first knee component away from the second knee component stretches or elongates the biasing member to provide a force that urges the knee components to move back to the first position,
wherein the second knee component comprises a cylindrical member having a first end for receiving a rod member and a second end that includes a pair of side walls surrounding a centrally located U-shaped recess, the extension member of the alignment mechanism comprises a central wall member extending between and away from the first and second surface portions on the second end of the cylindrical member of the first knee component, and the slot of the alignment mechanism is provided by the U-shaped recess on the second end of the cylindrical member of the second knee component.

15. The artificial knee of claim 14, wherein the first and second knee components are connected together by a horizontal bolt and nut that facilitates the rotation of the knee components, wherein the bolt passes through the central wall member of the cylindrical member of the first knee component and the side walls and U-shaped recess of the cylindrical member of the second knee component.

16. The artificial knee of claim 14, wherein the biasing member comprises a metal spring that is connected to each of the cylindrical members of the first and second knee components by a screw or bolt.

17. The artificial knee of claim 16, wherein the metal spring is provided within a sleeve to protect against pinching of fingers as the spring contracts from the second to first positions.

18. The artificial knee of claim 14, wherein the biasing member comprises an elastomeric member or rubber band.

19. The artificial knee of claim 14, wherein the first knee component comprises a first cylindrical member having an end for receiving a rod member, and the second knee component comprises a second cylindrical member having an end for receiving a rod member.

20. The artificial knee of claim 14, further comprising a locking member connecting the first and second knee components for retaining the knee components in the first position.

* * * * *